United States Patent [19]

Buckland

[11] Patent Number: 5,332,825

[45] Date of Patent: Jul. 26, 1994

[54] SINGLE VESSEL SYNTHESIS OF AMINOACETONITRILES

[75] Inventor: Paul R. Buckland, Rochester, N.Y.

[73] Assignee: Eastman Kodak Company, Rochester, N.Y.

[21] Appl. No.: 136,435

[22] Filed: Oct. 13, 1993

[51] Int. Cl.$^5$ .................. C07C 253/16; C07C 253; C07C 30; C07D 213/57

[52] U.S. Cl. .................. 546/330; 546/14; 549/4; 549/74; 549/75; 549/214; 549/491; 558/351; 558/408; 558/430; 558/432; 558/433; 558/434; 558/452; 556/417

[58] Field of Search .................. 558/351, 408, 452; 556/417; 549/75, 74, 4, 214, 491; 546/14, 330

[56] References Cited

U.S. PATENT DOCUMENTS

| | | | |
|---|---|---|---|
| 4,551,526 | 11/1985 | Mai et al. | 558/452 X |
| 4,611,076 | 9/1986 | Dong et al. | 558/351 |
| 4,694,103 | 9/1987 | Krepski et al. | 558/351 X |
| 5,169,973 | 12/1992 | Gibson et al. | 558/408 X |

OTHER PUBLICATIONS

"Facile Synthesis of α-Aminonitriles", Khuong Mai et al, *Tetrahedron Letters* vol. 25, No. 41, pp. 4583–4586, (1984).

"A Fast N-Substituted α-Aminonitrile Synthesis", Khuong Mai et al, *Synthetic Communications* 15 (2), 157–163 (1985).

*Primary Examiner*—Joseph Paul Brust
*Attorney, Agent, or Firm*—John D. Thallemer

[57] ABSTRACT

This invention relates to two processes for preparing aminoacetonitriles in one vessel under anhydrous conditions. Process I involves the steps of: (A) reacting trimethylsilyl cyanide and an aldehyde in a water miscible amide solvent to obtain a silyl blocked cyanohydrin solution; (B) adding a catalytic amount of water to the silyl blocked cyanohydrin solution from Step (A); and (C) passing ammonia through the solution to obtain an aminoacetonitrile. Process II involves the steps of: (A') reacting trimethylsilyl cyanide with an aldehyde in the absence of solvent to form a silyl blocked cyanohydrin; (B') adding a water miscible amide solvent to the silyl blocked cyanohydrin from Step (A') to obtain a solution; and (C') passing ammonia through the solution to obtain an aminoacetonitrile. Aminoacetonitriles are important intermediates in the preparation of amino acids, thiadiazoles, acylaminoacetonitriles, and imidazole derivatives.

4 Claims, No Drawings

SINGLE VESSEL SYNTHESIS OF AMINOACETONITRILES

FIELD OF THE INVENTION

This invention relates to two processes for preparing aminoacetonitriles in one vessel under anhydrous conditions. Process I involves the steps of: (A) reacting trimethylsilyl cyanide and an aldehyde in a water miscible amide solvent to obtain a silyl blocked cyanohydrin solution; (B) adding a catalytic amount of water to the silyl blocked cyanohydrin solution from Step (A); and (C) passing ammonia through the solution to obtain an aminoacetonitrile. Process II involves the steps of: (A') reacting trimethylsilyl cyanide with an aldehyde in the absence of solvent to form a silyl blocked cyanohydrin; (B') adding a water miscible amide solvent to the silyl blocked cyanohydrin from Step (A') to obtain a solution; and (C') passing ammonia through the solution to obtain an aminoacetonitrile. Aminoacetonitriles are important intermediates in the preparation of amino acids, thiadiazoles, acylaminoacetonitriles, and imidazole derivatives.

BACKGROUND OF THE INVENTION

Aminoacetonitriles have been prepared by reacting aldehydes with alkali metal cyanides followed by isolation of the cyanohydrin and subsequent reaction with ammonia in a suitable solvent. Isolation of the cyanohydrin can be difficult due to the solubility of cyanohydrin in aqueous medium. Moreover, isolation of the cyanohydrin is inconvenient and increases the risk of exposure to hydrogen cyanide.

Aminoacetonitriles have also been prepared without isolation of the cyanohydrin by the Strecker synthesis using an alkali metal cyanide and an ammonium salt under aqueous conditions. The Strecker synthesis, however, is not practical in cases where the aminoacetonitriles are subsequently used under nonaqueous conditions because it is difficult to isolate the aminoacetonitriles which are unstable and often water soluble.

In addition, aminoacetonitriles have been prepared by reacting aldehydes with trimethylsilyl cyanide in the presence of a catalytic amount of zinc iodide to obtain silyl blocked cyanohydrins which have been reacted with ammonia using protic solvents such as methanol to obtain aminoacetonitriles. Mai and Patil in an article entitled, "Facile Synthesis of alpha-Aminonitriles" which appeared in *TETRAHEDRON LETTERS*, Vol. 25, No. 41, pp. 4583–4586, 1984, disclose the preparation of aminonitriles by reacting trimethylsilyloxynitriles with various amines in methanol. On page 4583 of the article, Mai and Patil state that the amination step requires alcohol as a solvent. Moreover, they explicitly state that the amination did not proceed in an aprotic medium.

Mai and Patil in another article entitled, "A Fast N-Substituted alpha-Aminonitrile Synthesis" which appeared in SYNTHETIC COMMUNICATIONS, Vol. 15, No. 2, pp. 157–163, 1985, disclose the preparation of aminonitriles by reacting an aldehyde, an amine and trimethylsilyl cyanide at 100° C. for one minute. On page 158 of the article, Mai and Patil explicitly state that the silyloxynitrile does not react with an amine in an aprotic solvent even at elevated temperatures. In contrast to the articles by Mai and Patil, the present invention uses a water miscible amide solvent which is an aprotic solvent.

Mai and Patil also state in their article entitled, "A Fast N-Substituted alpha-Aminonitrile Synthesis" that the reaction is not applicable to the preparation of primary aminonitriles since gaseous ammonia does not react with the carbonyl compounds in the presence of aprotic solvents. In contrast, the present inventor has determined that gaseous ammonia reacts with silyl blocked cyanohydrin compounds in the presence of a water miscible amide solvent. Amide solvents are relatively involatile, thus, allowing passage of ammonia to occur over several hours without incurring significant solvent loss. Futhermore, clean conversion to the aminoacetonitriles occurs when amide solvents are used. The use of amide solvents allows the aminoacetonitriles to be converted to important intermediates such as thiadiazoles and acylamino derivatives. Other solvents are not as useful in these respects. For example, use of pyridine or acetonitrile as solvents in the amination step leads to the formation of by-products.

The processes of the present invention for preparing aminoacetonitriles and thereafter thiadiazole derivatives are represented as follows. The numbers appearing under each compound will be referred to throughout this document.

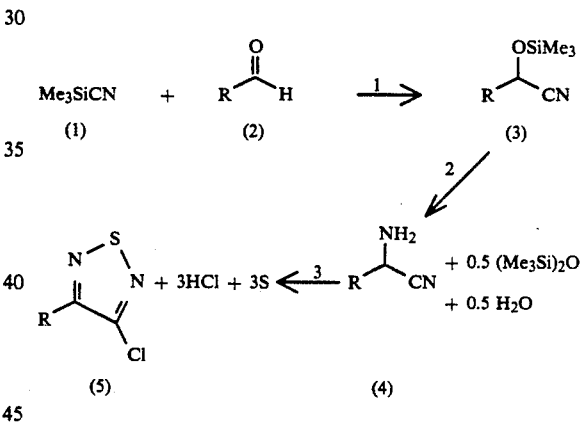

SUMMARY OF THE INVENTION

Accordingly, it is one object of the present invention to provide a process for preparing aminoacetonitriles.

Accordingly, it is another object of the invention to provide a process for preparing aminoacetonitriles in one vessel.

These and other objects are accomplished herein by a process, Process I, for preparing aminoacetonitriles in one vessel under anhydrous conditions, said process comprising:

(A) reacting trimethylsilyl cyanide and an aldehyde in water miscible amide solvent to obtain a silyl blocked cyanohydrin solution;

(B) adding a catalytic amount of water to the silyl blocked cyanohydrin solution from Step (A); and (C) passing ammonia through the solution to obtain an aminoacetonitrile.

The present invention is also directed to a process, Process II, for preparing aminoacetonitriles in one vessel under anhydrous conditions, said process comprising:

(A') reacting trimethylsilyl cyanide with an aldehyde the absence of solvent to form a silyl blocked cyanohydrin;

(B') adding a water miscible amide solvent to the silyl blocked cyanohydrin from Step (A') to obtain a solution; and (C') passing ammonia through the solution to obtain an aminoacetonitrile.

DESCRIPTION OF THE INVENTION

Process I for preparing aminoacetonitriles in one vessel under anhydrous conditions involves three steps. In the first step, Step (A), trimethylsilyl cyanide and an aldehyde are reacted in a water miscible amide solvent to obtain a silyl blocked cyanohydrin solution. The aldehyde has the general formula RCHO and is characterized by an unsaturated carbonyl group (C=O). The R group is selected from hydrogen, unsubstituted or substituted straight chain or branched $C_1$-$C_{20}$ alkyl, unsubstituted or substituted $C_3$-$C_8$ cycloalkyl, $C_3$-$C_8$ alkenyl, $C_3$-$C_8$ alkynyl, and $C_6$-$C_{14}$ aryl.

The unsubstituted and substituted $C_3$-$C_8$ cycloalkyl groups refer to cycloaliphatic hydrocarbon groups which contain 3 to 8 carbons in the ring, preferably 5 or 6 carbons, and these cycloalkyl groups substituted with one or two of $C_1$-$C_4$ alkyl, $C_1$-$C_4$ alkoxy, hydroxy or $C_1$-$C_4$ alkanoyloxy.

The $C_3$-$C_8$ alkenyl and $C_3$-$C_8$ alkynyl groups represent straight or branched chain hydrocarbon radicals containing 3 to 8 carbons in the chain and which contain a carbon-carbon double bond or a carbon-carbon triple bond, respectively.

The term "aryl" is used to include carbocyclic aryl groups containing up to fourteen carbons, e.g., phenyl and naphthyl, and those substituted with one or two groups selected from $C_1$-$C_4$-alkyl, $C_1$-$C_4$ alkoxy, $C_1$-$C_4$-alkoxycarbonyl, $C_1$-$C_4$-alkanoyloxy, $C_1$-$C_4$-alkanoylamino, halogen, cyano, $C_1$-$C_4$-alkylsulfonyl, $C_1$-$C_4$-alkylene-$(OH)_n$, O—$C_1$-$C_4$-alkylene-$(OH)_n$, —S—$C_1$-$C_4$-alkylene-(OH)hd n, —$SO_2$—$C_1$-$C_4$-alkylene-$(OH)_n$, —$CO_2$—$C_1$-$C_4$-alkylene-$(OH)_n$, $SO_2N$($R_{17}$)$C_1$-$C_4$-alkylene-$(OH)_n$, —$SO_2N$ ($C_1$-$C_4$-alkylene-OH)$_2$, —CON($R_{17}$)$C_1$-$C_4$-alkylene-$(OH)_n$, —CON($C_1$-$C_4$-alkylene-OH)$_2$, —N($SO_2C_1$-$C_4$-alkyl)-alkylene-$(OH)_n$ or —N($SO_2$ phenyl)-$C_1$-$C_4$-alkylene-$(OH)_n$; wherein n is one or two.

The term "aryl" is also used to include heterocyclic aryl groups such as a 5 or 6-membered heterocyclic aromatic ring containing one oxygen atom, and/or one sulfur atom, and/or up to three nitrogen atoms, said heterocyclic aryl ring optionally fused to one or two phenyl rings or another 5 or 6-membered heteroaryl ring. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl, and the like and those rings substituted with one or more substituents listed above in the definition of the term "aryl".

In addition, the term "aryl" includes arylene groups. The term "arylene" is used to represent a divalent carbocylic aryl hydrocarbon moiety containing up to fourteen carbons, e.g., o-, m- and p-phenylene, and those substituted with one or two groups selected from $C_1$-$C_4$-alkyl, $C_1$-$C_4$-alkoxy or halogen. Examples of suitable aldehydes for use in the process of this invention are: p-anisaldehyde, thiophene-2-carboxaldehyde, furan-2-carboxaldehyde, benzaldehyde, crotonaldehyde, trimethylacetaldehyde, acetaldehyde, 4-methylbenzaldehyde, 4-N,N-dimethylaminobenzaldehyde, 3-pyridinecarboxaldehyde, valeraldehyde, and 2-chlorobenzaldehyde. It is important to note that the use of 3-nitrobenzaldehyde as the aldehyde in the processes of the present invention does not result in the desired aminoacetonitrile.

In the second step, Step (B), a catalytic amount water is added to the silyl blocked cyanohydrin solution from Step (A). In the third step, Step (C), ammonia is passed through the solution to obtain an aminoacetonitrile. A catalytic amount of water must be added to the silyl blocked cyanohydrin before gaseous ammonia is applied otherwise no reaction occurs. Catalytic amount is a term which is understood by those skilled in the art. Preferably, 0.5 milligrams to 10 milligrams of water per gram of water miscible amide solvent, is added. There is no advantage to using more than a catalytic amount of water since Process I and Process II are conducted under anhydrous conditions and removal of water is difficult.

Process II for preparing aminoacetonitriles in one vessel under anhydrous conditions involves three steps. In the first step, Step (A'), trimethylsilyl cyanide is reacted with an aldehyde in the absence of solvent to form a silyl blocked cyanohydrin. In the second step, Step (B'), a water miscible amide solvent is added to the silyl blocked cyanohydrin from Step (A') to obtain a solution. In the third step, Step (C'), ammonia is passed through the solution to obtain an aminoacetonitrile. Unlike in Process I, no addition of water is required in Process II to facilitate the reaction between the silyl blocked cyanohydrin and ammonia.

Suitable water miscible amide solvents for use in the processes of the present invention are: N,N-dimethylformamide, N,N-diethylformamide, N,N-dimethylacetamide, N,N-diethylacetamide, N,N-dimethylpropionamide, N,N-diethylpropionamide and formamide. The water miscible amide solvent may also include a combination of such solvents. The use of pyridine or acetonitrile as solvents in the amination step leads to the formation of by-products.

Steps (A), (A'), (B), (B'), (C) and (C') in the processes of the present invention are conducted at a temperature from 20° C. to 50° C. A preferred temperature range is 30° C. to 40° C. Although higher temperatures may be employed, there is no advantage to conducting these reactions at higher temperatures. Moreover, at temperatures above 50° C., the aminolysis reaction requires the use of pressurized equipment.

The aminoacetonitriles are important intermediates in the preparation of amino acids, thiadiazoles, acylaminoacetonitriles, and imidazole derivatives. It is important to note, however, that aminoacetonitriles containing primary and secondary alkyl groups are not useful when the desired product is a thiadiazole. For example, where the aminoacetonitrile contains an n-butyl group, reaction with sulfur monochloride results in a complex mixture which does not contain any thiadiazole. Sulfur monochloride may be reacted with the aminoacetonitriles to obtain 3-chloro-4-substituted-1,2,5-thiadiazoles which are useful as intermediates in the synthesis of M1 selective muscarinic agonists, analgesics, antiglaucoma drugs and for treating Alzheimer's disease. Alternatively, the aminoacetonitriles may be reacted with heterocyclic acid chlorides to obtain car-

EXAMPLE 1

Preparation of 2-trimethylsilyloxy-2(3-pyridinyl)acetonitrile (3a, R=3-pyridyl)

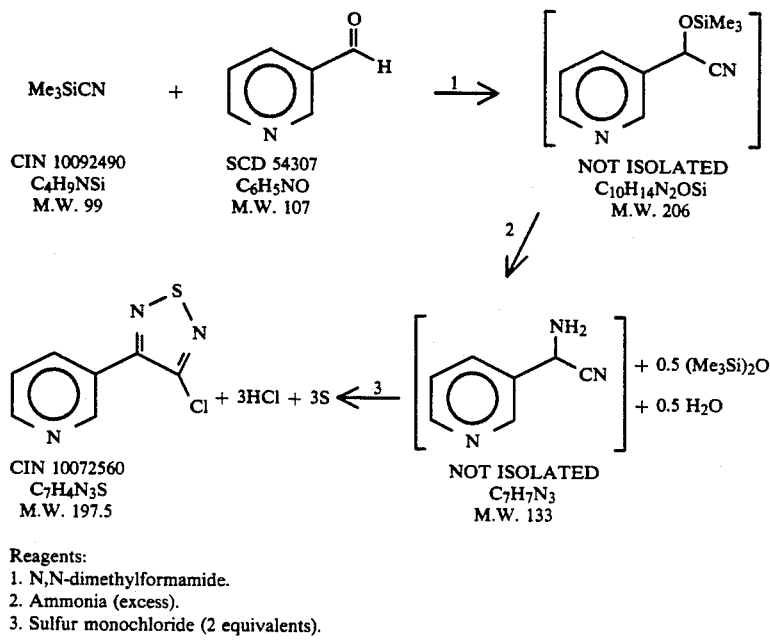

Reagents:
1. N,N-dimethylformamide.
2. Ammonia (excess).
3. Sulfur monochloride (2 equivalents).

boxamide derivatives which are useful as intermediates for agrochemical fungicides and microbicides.

Examples of agrochemical carboxamide intermediates derived from aminoacetonitriles include:

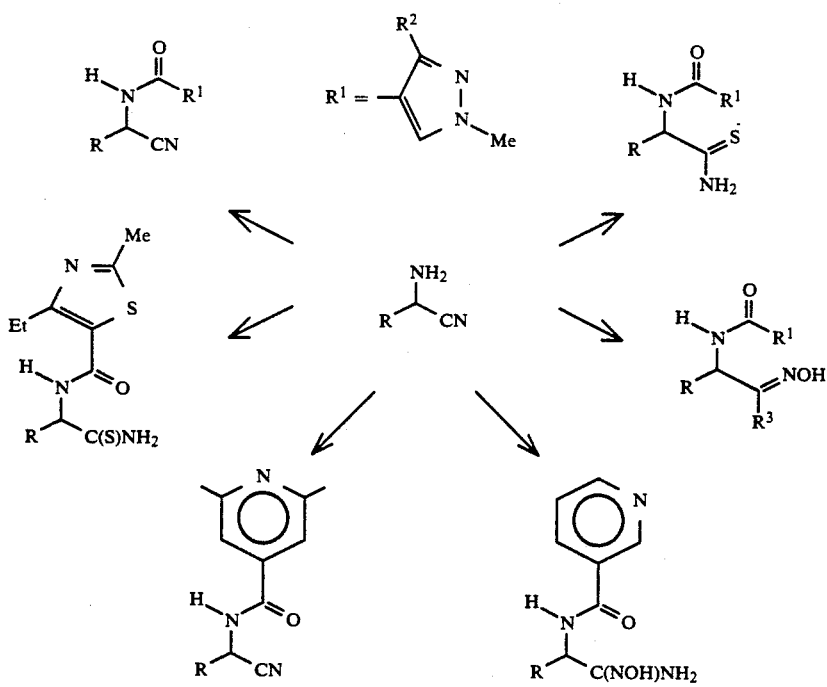

The process of the present invention will be further illustrated by a consideration of the following examples, which are intended to be exemplary of the invention. All parts and percentages in the examples are on a weight basis unless otherwise stated.

Trimethylsilyl cyanide, 25 grams, (0.2525 moles) was added in one portion to 150 grams (159 ml) N,N-dimethylformamide in a 500 ml three necked flask equipped with a nitrogen inlet, overhead stirrer and thermometer.

No exotherm or endotherm occurred on mixing of the cyanide and N,N-dimethylformamide. 3-Pyridinecarboxaldehyde, 24.61 grams, (0.23 moles) was added dropwise to the stirred mixture over 40 minutes. The temperature rose gradually from 26° C. to 42° C.

No catalyst was used in the reaction. Mixing of the reactants in the absence of solvent is very exothermic but does not appear to result in decomposition up to 100° C., of either the starting materials or product. The temperature of the yellow solution was allowed to fall to 26° C. over 1 hour and the mixture analyzed by NMR spectroscopy. The NMR spectrum was consistent with the desired product (CH at delta=5.4) and showed that no aldehyde starting material was present. Thus, the yield of the product was quantitative.

EXAMPLE 2

Preparation of 2-Amino-2-(3-pyridyl)acetonitrile (4a, R=3-pyridyl)

Ammonia was passed through the solution of 2-trimethylsilyloxy-2-(3-pyridinyl)acetonitrile (0.23 moles) prepared in Example 1, in N,N-dimethylformamide for 1 hour at room temperature, until the mixture became saturated. During this time, 5 grams (0.29 moles) of ammonia was absorbed and the temperature rose to 29° C., and the mixture became slightly more yellow. $CDCl_3$ was added to the reaction mixture in order to obtain NMR spectra of the N,N-dimethylformamide solutions. An NMR spectrum indicated that no reaction had taken place.

The temperature was increased to 33° C. and maintained for one hour. During this time, the rate of passage of ammonia was reduced so that excess gas was just able to escape through a nitrogen bubbler. No reaction took place. A catalytic amount of water, 150 mg, (0.008 mole) was added. The mixture changed color from yellow to reddish orange. Passage of ammonia was continued for one hour at 33° C. and the solution again analyzed by NMR spectroscopy. The spectrum indicated that conversion to an intermediate and product had begun (new methylene signals at 5.3 and 4.7 respectively). This suggested that the presence of water is necessary to catalyze the reaction. Any water in the N,N-dimethylformamide, would have been removed by initial reaction with trimethylsilyl cyanide. Subsequent passage of ammonia resulted in substantial reaction within 4 hours. The volatile by-product hexamethyldisiloxane was removed by the ammonia. Passage of ammonia was stopped and the mixture was stirred for 17 hours at a temperature of 30° C. to 33° C. The ratio of silyloxy starting material and cyanohydrin to aminonitrile product was approximately 5:1.5 indicating a 23% conversion. Ammonia was again passed through the solution and the temperature was maintained at 35° to 39° C. for 7 hours. Passage of ammonia was stopped and the mixture was stirred at 35° C. to 39° C. for 21 hours, after which time the reaction was complete.

The amount of conversion to product during the 7 hour period, based on the integrals for the methene signals due to starting material, intermediate and product, was found to be 23% (at t=0 hr), 38% (at t=2 hr) and 65% (at t=7 hr). A plot of this data suggested that had water been added at t=0 hr and ammonia gas passed throughout, the reaction would have been complete in approximately 11 hours. Excess ammonia was removed by application of water pump pressure for one hour. The solution was treated with $S_2Cl_2$.

EXAMPLE 3

Preparation of 3-(4-chloro-1,2,5-thiadiazol-3-yl) pyridine (5a, R=3-pyridyl)

Sulfur monochloride, 62.1 grams, (0.46 mole, 38 ml) was added dropwise with stirring over 1.5 hours, to the 2-Amino-2-(3-pyridyl)acetonitrile solution prepared in Example 2 which had been cooled to −5° C. (approx. 0.23 mole) in N,N-dimethylformamide. The mixture was stirred at 0° C. for one hour and then allowed to reach room temperature over 15 hours. The mixture was cooled to 0° C. and ethyl acetate, 150 ml, (135 grams) was added followed by addition of 70 grams of water over 15 minutes. A mixture of sodium hydroxide, 32.9 grams (0.82 mole) and 44.5 grams of water was added over one hour, while temperature was maintained at 5° to 10° C., to bring the pH of the mixture to 7.

The mixture was stirred for 15 minutes and then filtered through 40 grams of supercell to remove sulfur and salts. The residue was washed with 100 mt of ethyl acetate. A 20% sodium chloride solution, 200 grams, and 400 ml of toluene were added and the layers separated. It was necessary to add more solvents, because the solution was a dark orange brown making it impossible to see the liquid/liquid interface. The lower aqueous layer was discarded. The upper toluene/ethyl acetate layer was evaporated at 45° C. under reduced pressure to obtain 32 grams of crude product (70% overall yield from the aidehyde) as a brownish orange oil which solidified on standing overnight.

The NMR spectrum ($CDCl_3$) of the oil indicated that it contained approximately 87 weight percent of the desired product, the remainder being largely N,N-dimethylformamide. Heptanes, 180 ml, was added to 18 grams of the crude product and the mixture stirred and heated to 60° C. After 5 minutes, the clear yellow supernatant was removed from a small amount of dark insoluble liquid residue. The heptanes solution was cooled to 10° C. and the solid collected and dried to give 15.5 grams of 98% pure 3-(4-chloro-1,2,5-thiadiazol-3-yl)pyridine (60% yield) as a yellow solid. Elemental analysis determined: C,42.78; H, 2.19; N, 20.85; S, 15.99. $C_7H_4N_3S$ req. C, 42.54; H, 2.04; N, 21.26; S, 16.22%. The aqueous phase was extracted for a second time with 400 ml of toluene and gave only one gram of product. Thus, this second extraction was unnecessary.

One gram of the 3-(4-chloro-1,2,5-thiadiazol-3-yl)pyridinethiadiazole was dissolved in 5 grams of N,N-dimethylformamide and a solution of sodium chloride. 1.7 grams, and water, 6 grams, was added followed by 10 grams of toluene. After thorough mixing, the layers were allowed to separate and the bottom aqueous layer was removed. 11.5 grams of solution was recovered indicating that approximately 1.2 grams of N,N-dimethylformamide was extracted into the top toluene layer. The top layer was washed with 5 grams of 20% sodium chloride solution. The bottom layer was removed and found to weigh 5.8 grams indicating that most of the N,N-dimethylformamide had been removed. The top toluene layer was dried with 500 mg of sodium sulfate and evaporated to give the product as a cream solid (1 gram). Clearly, toluene is a very effective solvent for extracting the product from N,N-dimethylformamide/sodium chloride/water mixtures. However, the toluene extract must be washed to ensure removal of N,N-dimethylformamide.

EXAMPLES 4–6

Trimethylsilyl blocked cyanohydrins (3b, R=3-nitrophenyl), (3c, R=n-butyl) and (3d, R=2-chlorophenyl)

Trimethylsilyl cyanide (1), 4.95 grams, (0.05 mole) was added in one portion to 30 ml of N,N-dimethylformamide in a 100 ml three necked flask equipped with a nitrogen inlet, stirrer bar and thermometer. No exotherm or endotherm occurred on mixing of the cyanide and N,N-dimethylformamide. The aldehyde (2), 0.05 moles, was added dropwise to the stirred mixture over 5 minutes. After reaction was complete as evidenced by I.R. and NMR spectroscopy, the product was treated with ammonia. After 2 hours I.R. analysis (nitrile region) of the mixtures showed the absence of trimethylsilyl cyanide (2188 cm$^{-1}$), indicating that reaction was complete. The NMR spectra (CDCl$_3$) were consistent with formation of the desired products. No aldehyde starting material was present, which implies that the yield of the product was quantitative for these examples.

| ALDEHYDES USED TO PREPARE CYANOHYDRINS | | |
|---|---|---|
| CHEMICAL NAME | M.W. | GRAMS |
| 3 NITROBENZALDEHYDE (2b)* | 151 | 7.55 |
| VALERALDEHYDE (2c) | 86 | 4.3 |
| 2-CHLOROBENZALDEHYDE (2d) | 140.5 | 7.0 |

*Dissolved in N,N-dimethylformamide (5 ml) and added to trimethylsilyl cyanide in N,N-dimethylformamide (25 ml)

EXAMPLES 7-14

Preparation of Trimethylsilyl Blocked Cyanohydrins (3e, R=4-methoxyphenyl), (3f, R=2-thienyl), (3g, R=2-furanyl), (3h, R=phenyl), (3i, R=MeCH=CH—), (3j, R=t-Bu), (3k, R=4-methylphenyl), (3l, R=4-N,N-dimethylaminophenyl)

Trimethylsilyl cyanide, 4.95 grams, (0.05 mole) was added to a 100 ml three neck flask equipped with a nitrogen inlet, stirrer bar and thermometer, followed by the 0.05 moles of the aldehyde as set forth in Table II. N,N,-dimethylaminobenzaldehyde (21), a solid, and trimethylsilyl cyanide were warmed to produce a solution. No reaction occurred. Zinc iodide, 0.1 gram was added at which point all the mixtures became hot and required cooling in order to keep the temperature below 70° C. The mixtures were then allowed to cool to room temperature and kept for two additional hours before analysis. Reaction was complete as evidenced by I.R. and NMR spectroscopy. Anisaldehyde required 0.25 grams of trimethylsilyl cyanide and heat at 100° C. for 30 minutes to complete the reaction.

I.R. analysis (0.025 mm solution cell) was used to monitor disappearance of the aldehyde carbonyl band. The NMR spectra (N,N-dimethylformamide/CDCl$_3$,) were consistent with formation of the desired products. No aldehyde starting material was present, which implies that the yield of the product was quantitative for these examples. N,N-Dimethylformamide was added and the product was treated with ammonia.

| ALDEHYDES USED TO PREPARE BLOCKED CYANOHYDRINS(3) | | |
|---|---|---|
| CHEMICAL NAME | M.W. | GRAMS |
| p-ANISALDEHYDE (2e) | 136 | 6.8 |
| THIOPHENE-2-CARBOXALDEHYDE (2f) | 112 | 5.6 |
| FURAN-2-CARBOXALDEHYDE (2g) | 96 | 4.8 |
| BENZALDEHYDE (2h) | 86 | 5.3 |
| CROTONALDEHYDE (2i) | 70 | 3.5 |
| TRIMETHYLACETALDEHYDE (2j) | 86 | 4.3 |
| 4-METHYLBENZALDEHYDE (2k) | 120 | 6.0 |
| 4-N,N-DIMETHYLAMINO-BENZALDEHYDE (21) | 149 | 7.45 |

Spectroscopic data for compounds (3a): R=3-pyridyl, (3b): R=3-nitrophenyl, (3c): R=n-butyl, (3d): R=2-chlorophenyl, (3e): R=4-methoxyphenyl, (3f): R=2-thienyl, (3g): R=2-furanyl, (3h): R=phenyl, (3i): R=4-MeCH=CH—, (3j): R=t-Bu, (3k): R=4-methylphenyl, (31) R=4-N,N-dimethylaminophenyl, was as follows:

| $^1$H NMR SPECTRAL DATA FOR SILYL BLOCKED CYANOHYDRINS | |
|---|---|
| COMPOUND | CHEMICAL SHIFT (ppm)* |
| 3a | 0.0(s, 9H), 5.4(s, H), 7.1(m, 1H), 7.6(m, 1H), 8.4(m, 1H), 8.5(d, 1H) |
| 3b | 0.0(s, 9H), 5.5(s, 1H), 7.3(t, 1H), 7.5(t, 1H), 7.8(d, 1H), 8.0(s, 1H) |
| 3c | −0.1(s, 9H), 0.6(t, 3H), 1.1(m, 4H), 1.4(m, 2H), 4.1(t, 1H) |
| 3d | −0.3(s, 9H), 5.3(s, 1H), 6.9(m, 3H), 7.2(m, 2H) |
| 3e | 0.2(s, 9H), 3.8(s, 3H), 5.4(s, 1H), 6.9(d, 2H), 7.4(d, 2H) |
| 3f | 0.3(s, 9H), 5.7(s, 1H), 7.0(dd, 1H), 7.2(d, 1H), 7.4(d, 1H) |
| 3g | 0.2(s, 9H), 5.5(s, 1H) 6.4(t, 1H), 6.5(d, 1H), 7.5(d, 1H) |
| 3h | 0.2(s, 9H), 5.5(s, 1H), 7.4 to 7.5 (m, 5H) |
| 3i | 0.2(s, 9H), 1.8(m, 1H), 5.6(m, 1H), 6.0(m, 1H) |
| 3j | 0.3(s, 9H), 1.1(s, 9H), 4.0(s, 1H) |
| 3k | 0.3(s, 9H), 2.4(s, 3H), 5.5(s, 1H), 7.2(d, 1H), 7.4(d, 1H) |
| | 0.3(s, 9H), 3.0(s, 6H), 5.4(s, 1H), 6.7(d, 2H), 7.3(d, 2H) |

*Compounds 3a to 3d used 1:1 N,N-dimethylformamide/CDCl$_3$ as the solvent and Compounds 3e to 3g used CDCl$_3$ as the solvent.

EXAMPLES 15-24

Preparation of Aminoacetonitriles (4c, R=n-butyl), (4d, R=2-chlorophenyl), (4e, R=4-methoxyphenyl), (4f, R=2-thienyl), (4g, R=2-furanyl), (4h, R=phenyl), (3i, R=MeCH=CH—), (3j, R=t-Bu), (3k, R=4-methylphenyl), (31, R=4-N,N-dimethylaminophenyl).

A catalytic amount of water, 0.1 grams, (0.0056 mole) was added to a solution of the silyl blocked cyanohydrin (assume 0.05 mole) in 30 ml of N,N-dimethylformamide. (It is necessary to add water in order to ensure subsequent reaction with ammonia.) Ammonia was passed through the solution for 24 to 48 hours at room temperature so that excess gas was just able to escape through a nitrogen bubbler. The mixture was analyzed by NMR spectroscopy to determine that the reaction was complete. CDCl$_3$ was added to the reaction mixture in order to obtain NMR spectra of the N,N-dimethylformamide solutions. The spectra indicated that clean conversion to the product was complete in 24 to 48 hours, except for the nitro-substituted material (3b). Excess ammonia was removed by application of water pump pressure for 1 hour. The resulting solution of aminoacetonitrile was treated with sulfur monochloride or a carboxylic acid chloride.

Spectroscopic data for compounds (4a): 3-pyridyl, (4b): 3-nitrophenyl, (4c): n-butyl, (4d): 2-chlorophenyl, (4e): 4-methoxyphenyl, (4f): 2-thienyl, (4g): 2-furanyl, (4h): phenyl, (3i): MeCH=CH—, (3j): t-Bu, (3k): 4-methylphenyl, (31): 4-N,N-dimethylaminophenyl, were as follows:

| | ¹H N.M.R. SPECTRAL DATA FOR AMINOACETONITRILES | |
|---|---|---|
| COMPOUND | CHEMICAL SHIFT (ppm)** | |
| 4a | 4.8(s, 1H), 7.1(m, 1H), 7.7(m, 1H), 8.4(m, 1H), 8.6(d, 1H) | |
| 4b | Spectrum inconsistent with desired product | |
| 4c | 0.3(t, 3H), 0.8(m, 4H), 1.1(m, 2H), 1.4 (br.s, NH2/NH3), 3.1(t, 1H) | |
| 4d | 2.0(br.s, NH2/NH3), 4.7(s, 1H), 6.8(m, 3H), 7.2(m, 2H) | |
| 4e | 2.1(br.s, NH2), 3.4(s, 3H), 4.6(s, 1H), 6.8(d, 2H), 7.1(d, 2H) | |
| 4f | 2.1(br.s, NH2/NH3), 4.8(s, 1H), 6.6(dd, 1H), 6.8(d, 1H), 7.0(d, 1H) | |
| 4g | 2.2(br.s, NH2/NH3), 4.7(s, 1H), 6.1(t, 1H), 6.2(d, 1H), 7.2(d, 1H) | |
| 4h | 1.9(br.s, NH2/NH3), 4.5(s, 1H), 7.0(m, 3H), 7.1(m, 2H) | |
| 4i | 1.5(m, 3H), 2.0(br.s, NH2/NH3), 4.0(m, 1H), 5.3(m, 1H), 5.7(m, 1H) | |
| 4j | 0.6(s, 9H), 1.3(br.s, NH2/NH3), 3.0(s, 1H) | |
| 4k | 2.1(br.s. CH3/NH2/NH3), 4.7(s, 1H), 7.0(d, 2H), 7.2(d, 2H) | |
| 4l | 1.9(br.s, NH2/NH3), 4.6(s), 6.4(d), 7.1(d) | |

**Solvent 1:1 N,N-dimethylformamideCDCl₃

EXAMPLES 25-29

3-Chloro-4-substituted-1,2,5-thiadiazoles (5d, R=2-chlorophenyl), (5e, R=4-methoxyphenyl), (5f, R=2-thienyl), (5h, R=phenyl), (5j, R=t-Bu-).

Sulfur monochloride, 20.25 grams, (0.15 mole, 12 ml) was added dropwise over 30 minutes with stirring, to previously cooled (−10° C.) solutions of the aminonitriles (approx. 0.05 mole) in 30 ml of N,N-dimethylformamide so that the temperature was maintained at −10° to 0° C. The mixture was stirred at 0° C. to 5° C. for 1 hour and then allowed to stir at room temperature for 24 hours. Toluene (30 ml, 26 grams) was added followed by addition of 25 grams of ice cold water. The mixture was stirred for a further 15 minutes and then filtered through 2 grams of supercell to remove sulfur. The residue was washed with 10 ml, 8.7 grams of toluene. The layers were separated and the lower aqueous layer was discarded. The upper toluene layer was washed with a 12.5% sodium chloride solution in water and the bottom aqueous layer discarded. The washing was repeated. The upper toluene layer was dried over 8 grams of sodium sulfate and the solvent evaporated at 40° C. under reduced pressure (water pump) to obtain the crude product (5) as a brownish orange oil which was analyzed by NMR spectroscopy and gas chromatography. The ¹H and ¹³C NMR spectra (CDCl₃) of the oils were consistent with the structure of the desired products. G.C. analysis indicated that the products were 77 to 98% pure.

Spectroscopic data for compounds (5a) :- 3-pyridyl, (5d) :- 2-chlorophenyl, (5e) :- 4-methoxyphenyl, (5f) :- 2-thienyl, (5h) :- phenyl and (5j) :- R =t-Bu- were as follows:

| | ¹³C NMR SPECTRAL DATA FOR 3-CHLOROTHIADIAZOLES (5) |
|---|---|
| COMPOUND | CHEMICAL SHIFT (ppm)*** |
| 5a | 123, 127, 136, 149, 144 (C=N), 151, 155(ClC=N) |
| 5d | 127, 130, 130, 131, 131, 134, 146(C=N), 157(ClC=N) |
| 5e | 56(CH₃O), 114, 124, 130, 143(C=N), 158(ClC=N), 161 |
| 5f | 129, 129, 130, 133, 142(C=N), 152(ClC=N) |
| 5h | 128, 129, 130, 131, 144(C=N), 158(ClC=N) |
| 5j | 28, 36, 143(C=N), 167(ClC=N) |

| | ¹H NMR SPECTRAL DATA FOR 3-CHLOROTHIADIAZOLES (5) |
|---|---|
| COMPOUND | CHEMICAL SHIFT (ppm)*** |
| 5a | 7.5(q, 1H), 8.3(dt, 1H), 8.7(br.d, 1H), 9.2(br.s, 1H) |
| 5d | 7.3 to 7.5(m) |
| 5e | 3.9(s, 3H), 7.0(d, 2H), 8.0(d, 2H) |
| 5f | 7.2(dd, 3H), 7.5(dd, 1H), 8.0(dd, 1H) |
| 5h | 7.5(m, 3H), 8.0(d, 2H) |
| 5j | 1.5(s) |

| | YIELD AND PURITY (G.C) OF 3-CHLOROTHIADIAZOLES (5) | | | |
|---|---|---|---|---|
| COMPOUND | MOL. FORM. | MW | YIELD (%) | PURITY(G.C.) |
| 5d | C₈H₄Cl₂N₂S | 231 | 96 | 98 |
| 5e | C₉H₇ClN₂OS | 226.5 | 71 | 79 |
| 5f | C₆H₃ClN₂S₂ | 202.5 | 37 | 79 |
| 5h | C₈H₅ClN₂S | 196.5 | 76 | 9 |
| 5j | C₆H₉ClN₂S | 176.5 | 50 | 77 |

***Solvent CDCl₃

EXAMPLE 30

N-(CYANO-2-THIENYLMETHYL)-3-PYRIDINECARBOXAMIDE

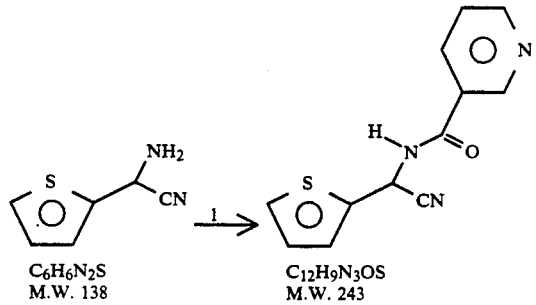

Reagents: Nicotinyl chloride, triethylamine.

Triethylamine, 10.1 grams, (0.1 mole) was added to a solution of amino-2-thienylacetonitrile (0.05 mole) in 15 ml of N,N-dimethylformamide. The mixture was cooled to 0° C. and 8.9 grams of nicotinyl chloride hydrochloride (0.05 mole) was added. After stirring at 0° C. for 1 hour, the mixture was stirred at room temperature for an additional 24 hours. Water, 100 ml, was added and the solid was collected. The solid was boiled with water and the supernatant was decanted. Cooling of this solution gave a yellow solid whose NMR spectrum was consistent with the desired product, m.p. 136° to 137° C.

¹H NMR data (solvent d6-DMOS); ppm: 6.7(d, 1H, H$^a$), 7.1(dd, 1H, H$^b$), 7.3 (m, 1H, H$^c$), 7.55(dd, 1H, H$^d$), 7.65(dd, 1H, H$^3$), 8.3(dt, 1H, H$^f$), 8.8(dd, 1H, H$^g$), 9.1(d, 1H, H$^h$), 10.1(d, 1H, H$^i$).

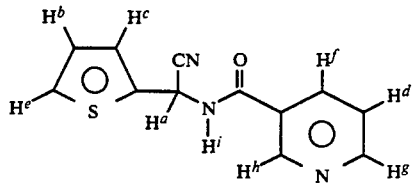

Many variations will suggest themselves to those skilled in this art in light of the above detailed description. All such obvious modifications are within the full intended scope of the appended claims.

What is claimed is:

1. A process for preparing aminoacetonitriles under anhydrous conditions comprising the steps of:

(A) reacting trimethylsilyl cyanide and an aldehyde having the formula RCHO in a water miscible amide solvent to obtain a silyl blocked cyanohydrin solution, wherein R is selected from the group consisting of hydrogen, $C_1$–$C_{20}$ alkyl, $C_3$–$C_8$ cycloalkyl, $C_3$–$C_8$ alkenyl, $C_3$–$C_8$ alkynyl, and $C_6$–$C_{14}$ aryl, excluding 3-nitrobenzaldehyde, and the water miscible amide solvent is selected from the group consisting of N,N-dimethylformamide, N,N-diethylformamide, N,N-dimethylacetamide, N,N-diethylacetamide, N,N-dimethylpropionamide, N,N-diethylpropionamide, formamide, and combinations thereof;

(B) adding 0.5 milligrams to 10 milligrams of water per gram of water miscible amide solvent to the silyl blocked cyanohydrin solution from step (A); and (C) passing ammonia through the solution from step (B) to obtain an aminoacetonitrile, provided steps (A), (B), and (C) are conducted at a temperature of 20° C. to 50° C., and further provided that steps (A), (B), and (C) are conducted in the same reaction vessel wherein the silyl blocked cyanohydrin is not isolated and wherein anhydrous means no water is present except that added in step (B).

2. A process for preparing aminoacetonitriles under anhydrous conditions comprising the steps of:

(A) reacting trimethylsilyl cyanide and an aldehyde in N,N-dimethylformamide to obtain a silyl blocked cyanohydrin solution, wherein the aldehyde is selected from the group consisting of p-anisaldehyde, thiophene-2-carboxaldehyde, furan-2-carboxaldehyde, benzaldehyde, crotonaldehyde, trimethylacetldehyde, acetaldehyde, 4-methylbenzaldehyde, 4-N,N-dimethylaminobenzaldehyde, 3-pyridinecarboxaldehyde, valeraldehyde, and 2-chlorobenzaldehyde;

(B) adding 0.5 milligrams to 10 milligrams of water per gram of water miscible amide solvent to the silyl blocked cyanohydrin solution from step (A); and (C) passing ammonia through the solution from step (B) to obtain an aminoacetonitrile, provided steps (A), (B), and (C) are conducted at a temperature of 30° C. to 40° C., and further provided that steps (A), (B), and (C) are conducted in the same reaction vessel wherein the silyl blocked cyanohydrin is not isolated and wherein anhydrous means no water is present except that added in step (B).

3. A process for preparing aminoacetonitriles under anhydrous conditions comprising the steps of:

(A') reacting trimethylsilyl cyanide with an aldehyde having the formula RCHO in the absence of a solvent to form a silyl blocked cyanohydrin, wherein R is selected from the group consisting of hydrogen, $C_1$–$C_{20}$ alkyl, $C_3$–$C_8$ cycloalkyl, $C_3$–$C_8$ alkenyl, $C_3$–$C_8$ alkynyl, and $C_6$–$C_{14}$ aryl, excluding 3-nitrobenzaldehyde;

(B') adding a water miscible amide solvent to the silyl blocked cyanohydrin formed in step (A') to obtain a solution, wherein the water miscible amide solvent is selected from the group consisting of N,N-dimethylformamide, N,N-diethylformamide, N,N-dimethylacetamide, N,N-diethylacetamide, N,N-dimethylpropionamide, N,N-diethylpropionamide, formamide, and combinations thereof; and (C') passing ammonia through the solution from step (B') to obtain an aminoacetonitrile, provided steps (A'), (B'), and (C') are conducted at a temperature of 20° C. to 50° C., and further provided that steps (A'), (B'), and (C') are conducted in the same reaction vessel wherein the silyl blocked cyanohydrin is not isolated.

4. A process for preparing aminoacetonitriles under anhydrous conditions comprising the steps of:

(A') reacting trimethylsilyl cyanide with an aldehyde in the absence of a solvent to form a silyl blocked cyanohydrin, wherein the aldehyde is selected from the group consisting of p-anisaldehyde, thiophene-2-carboxaldehyde, furan-2-carboxaldehyde, benzaldehyde, crotonaldehyde, trimethylacetaldehyde, acetaldehyde, 4-methylbenzaldehyde, 4-N,N-dimethylaminobenzaldehyde, 3-pyridinecarboxaldehyde, valeraldehyde, and 2-chlorobenzaldehyde;

(B') adding N,N-dimethylformamide to the silyl blocked cyanohydrin formed in Step (A') to obtain a solution; and (C') passing ammonia through the solution from step (B') to obtain an aminoacetonitrile, provided steps (A'), (B'), and (C') are conducted at a temperature of 30° C. to 40° C., and further provided that steps (A'), (B'), and (C') are conducted in the same reaction vessel wherein the silyl blocked cyanohydrin is not isolated.

* * * * *